United States Patent [19]

Kim et al.

[11] Patent Number: 5,502,200
[45] Date of Patent: Mar. 26, 1996

[54] REACTIVE THIOPHOSPHATE DERIVATIVES OF THIA(DIA)ZOLE ACETIC ACID AND PROCESS FOR PREPARING THE SAME

[75] Inventors: Sung Kyum Kim; Jong C. Lim; Tae S. Kwon; Bong J. Park, all of Youseong; Woo H. Kim, Seo, all of Rep. of Korea

[73] Assignee: Lucky, Ltd., Rep. of Korea

[21] Appl. No.: 223,756

[22] Filed: Apr. 6, 1994

[30] Foreign Application Priority Data

Apr. 10, 1993 [KR] Rep. of Korea ............... 936008

[51] Int. Cl.⁶ .................................................. C07F 9/02
[52] U.S. Cl. ................................................... 548/119
[58] Field of Search ...................................... 548/119

[56] References Cited

U.S. PATENT DOCUMENTS

| | | | |
|---|---|---|---|
| 4,478,749 | 10/1984 | Koster et al. | 260/245.4 |
| 4,506,076 | 3/1985 | Kamiya et al. | 548/119 |
| 5,278,152 | 1/1994 | Peyman et al. | 514/76 |

FOREIGN PATENT DOCUMENTS

| | | | |
|---|---|---|---|
| 0034760 | 9/1981 | European Pat. Off. . | |
| 0061765 | 10/1982 | European Pat. Off. . | |
| 0377987 | 7/1990 | European Pat. Off. . | |
| 175196 | 10/1982 | Japan | 548/119 |
| 2033390 | 5/1980 | United Kingdom . | |

Primary Examiner—Joseph K. McKane
Attorney, Agent, or Firm—Birch, Stewart, Kolasch & Birch

[57] ABSTRACT

The present invention relates to a novel reactive thiophosphate derivative of thia(dia)zole acetic acid which can be very effectively used in the preparation of β-lactam antibiotics, and which is represented by the following general formula (I):

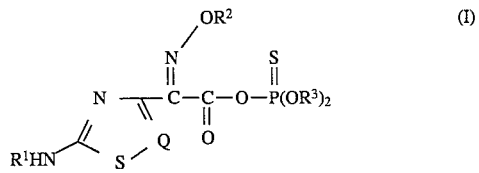

in which $R^1$ represents hydrogen or an amino-protecting group;

$R^2$ represents hydrogen, $C_1$–$C_4$ alkyl, or —$C(R^a)(R^b)CO_2R^c$, wherein $R^a$ and $R^b$ are identical or different from each other and represent hydrogen or $C_1$–$C_4$ alkyl, or $R^a$ and $R^b$ together with a carbon atom to which they are bound can form a $C_3$–$C_7$ cycloalkyl group and $R^c$ is hydrogen or a carboxy-protecting group;

$R^3$ represents $C_1$–$C_4$ alkyl or phenyl or $R^3$ together with an oxygen atom and a phosphorus atom to which it is bound can form a 5- or 6-membered heterocyclic ring; and Q represents N or CH, and to a process for preparing the same.

4 Claims, No Drawings

REACTIVE THIOPHOSPHATE DERIVATIVES OF THIA(DIA)ZOLE ACETIC ACID AND PROCESS FOR PREPARING THE SAME

BACKGROUND OF INVENTION

1. Field of Invention

The present invention relates to a novel reactive organic acid derivative which can be very effectively used in preparation of β-lactam antibiotics. Specifically, the present invention relates to a novel reactive thiophosphate derivative of thia(dia)zole acetic acid represented by the following general formula (I):

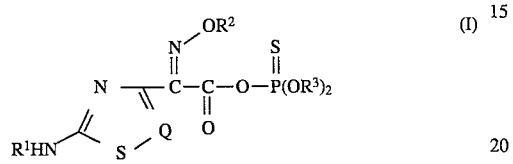

in which $R^1$ represents hydrogen or an amino-protecting group;

$R^2$ represents hydrogen $C_1$–$C_4$ alkyl, or —C($R^a$)($R^b$)CO$_2R^c$, wherein $R^a$ and $R^b$ are identical or different from each other and represent hydrogen or $C_1$–$C_4$ alkyl, or $R^a$ and $R^b$ together with a carbon atom to which they are bound form a $C_3$–$C_7$ cycloalkyl group, and $R^c$ is hydrogen or a carboxy-protecting group;

$R^3$ represents $C_1$–$C_4$ alkyl or phenyl, or $R^3$ together with an oxygen atom and a phosphorus atom to which it is bound form a 5- or 6-membered heterocyclic ring; and Q represents N or CH.

The present invention also relates to a process for preparation of the reactive derivative of formula (I), as defined above.

2. Background Art

Numerous methods for preparation of β-lactam antibiotics have been disclosed in early published references and patent specifications. However, such prior methods prepare the β-lactam antibiotic compound commonly starting from an organic acid having the following general formula (II) by converting it into its reactive derivative which is then subjected to an acylation reaction with an amino group of the β-lactam nucleus.

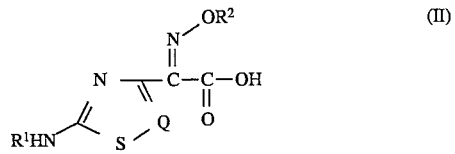

In the above formula (II), $R^1$, $R^2$ and Q are defined as previously described.

The reactive derivative of the compound of formula (II) which has been conventionally used in the above-mentioned prior methods includes an acid chloride, a reactive ester, a reactive amide, a mixed acid anhydride and the like. However, such reactive derivatives have some disadvantages as mentioned below. Specifically, the reactive derivative in the form of an acid chloride or a mixed acid anhydride should be prepared under stringent reaction conditions and further is unstable, so that it might be used in situ for the acylation reaction without isolation. This may be the major reason for the formation of by-products. Furthermore, when the reactive derivative of the compound of formula (II) is in the form of a reactive ester and a reactive amide, it has also disadvantages in that both the yield and the reactivity of such reactive derivatives are very low and the acylation reaction requires a long reaction time due to their low reactivity and, further, the reaction by-products, for example, a hydroxy derivative such as 1-hydroxybenzotriazole and a thiol derivative such as 2-mercaptobenzothiazole, can be hardly removed.

In addition, Japanese Laid-open Patent Publication No. (Sho) 57-175196, pages 891–892, discloses diphenyloxophosphoryl (Z)-(2-aminothiazol-4-yl)methoxyimino acetate of formula (A), which can be prepared from (Z)-(2-aminothiazol-4-yl)methoxyimino acetic acid and a diphenyl chlorophosphate derivative.

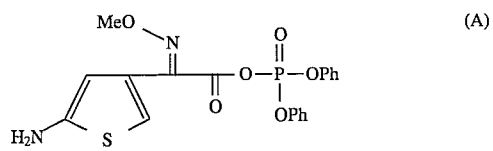

However, the compound of formula (A) is an unstable reactive mixed acid anhydride, which cannot be isolated, and therefore can affect adversely the reaction in the next step.

Accordingly, the present inventors have continuously studied to discover a method which can solve the problems involved in the known reactive derivatives as previously described. As a result, we have discover that a novel reactive derivative having a suitable reactivity and stability can be prepared from the organic acid of formula (II) above and a chlorothiophosphate derivative substantially in a convenient manner and in a high yield and then completed the present invention.

Therefore, it is an object of the present invention to provide a novel reactive thiophosphate derivative of thia(dia)zole acetic acid of formula (I), as defined above, which can be very effectively used for preparation of the β-lactam antibiotic compound.

It is a further object of this invention to provide a process for preparing the novel reactive derivative of formula (I).

The foregoing has outlined some of the more pertinent objects of the present invention. These objects should be construed to be merely illustrative of some of the more pertinent features and applications of the invention. Many other beneficial results can be obtained by applying the disclosed invention in a different manner or modifying the invention within the scope of the disclosure. Accordingly, other objects and a more thorough understanding of the invention may be had by referring to the disclosure of invention, in addition to the scope of the invention defined by the claims.

DISCLOSURE OF INVENTION

In one aspect, the present invention relates to a novel reactive thiophosphate derivative of thia(dia)zole acetic acid which can be represented by the following general formula (I):

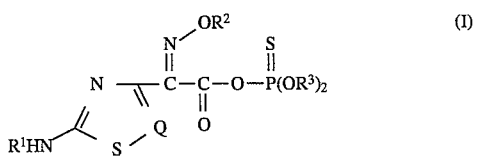

in which $R^1$ represents hydrogen or an amino-protecting group;

$R^2$ represents hydrogen, $C_1$–$C_4$ alkyl, or —$C(R^a)(R^b)CO_2R^c$, wherein $R^a$ and $R^b$ are identical or different from each other and represent hydrogen or $C_1$–$C_4$ alkyl, or $R^a$ and $R^b$ together with a carbon atom to which they are bound form a $C_3$–$C_7$ cycloalkyl group, and $R^c$ is hydrogen or a carboxy-protecting group;

$R^3$ represents $C_1$–$C_4$ alkyl or phenyl, or $R^3$ together with an oxygen atom and a phosphorus atom to which it is bound can form a 5- or 6-membered heterocyclic ring; and Q represents N or CH.

In another aspect, the present invention relates to a process for preparation of the reactive organic acid derivative of formula (I), as defined above, characterized in that an organic acid having the following general formula (II):

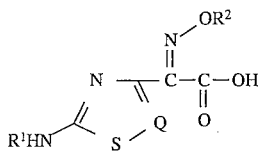

(II)

in which $R^1$, $R^2$ and Q are defined as previously described, is reacted with a chlorothiophosphate derivative having the following general formula (III):

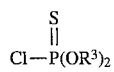

(III)

in which $R^3$ is defined as previously described, in a solvent in the presence of a base and a catalyst.

Preferably, in the compound of formula (I) according to the present invention, $R^1$ represents hydrogen or triphenylmethyl, $R^2$ represents hydrogen, methyl, ethyl or t-butoxycarbonylisopropyl and $R^3$ represents methyl, ethyl or phenyl.

More preferable compounds of formula (I) according to the present invention are as follows:

diethylthiophosphoryl (Z)-(2-aminothiazol-4-yl)methoxyimino acetate, diethylthiophosphoryl (Z)-(2-triphenylmethylaminothiazol-4-yl)methoxyimino acetate, diethylthiophosphoryl (Z)-(2-aminothiazol-4-yl)-2-(t-butoxycarbonyl)isopropoxyimino acetate, diethylthiophosphoryl (Z)-(2-aminothiazol-4-yl)ethoxyimino acetate, diethylthiophosphoryl (Z)-(2-triphenylmethylaminothiazol-4-yl)ethoxyimino acetate, diethylthiophosphoryl (Z)-(2-triphenylmethylaminothiazol-4-yl)-2-(t-butoxycarbonyl)isopropoxyimino acetate, or diethylthiophosphoryl (Z)-(3-amino-1,2,4-thiadiazol-5-yl)ethoxyimino acetate.

The process for preparing the reactive derivative of formula (I) according to the present invention can be represented by the following reaction scheme:

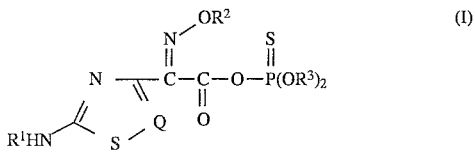

(I)

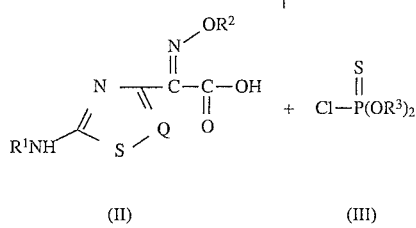

(II)          (III)

in which $R^1$, $R^2$, $R^3$ and Q are defined as previously described.

In the above reaction scheme, an amino-protecting group for $R^1$ denotes a conventional amino-protecting group such as acyl, substituted or unsubstituted ar(lower)alkyl (e.g. benzyl, diphenylmethyl, triphenylmethyl, 4-methoxybenzyl, etc.), halo (lower) alkyl (e.g. trichloromethyl, trichloroethyl, etc.), tetrahydropyranyl, substituted phenylthio, substituted alkylidene, substituted aralkylidene, substituted cycloalkylidene, and the like. A suitable acyl as the amino-protecting group may be an aliphatic acyl group or an acyl group having an aromatic or heterocyclic moiety. Such acyl group includes, for example, lower alkanoyl having 1 to 6 carbon atoms (e.g. formyl, acetyl, etc.), alkoxycarbonyl having 2 to 6 carbon atoms (e.g. methoxycarbonyl, ethoxycarbonyl, etc.), lower alkanesulfonyl (e.g. methanesulfonyl, ethanesulfonyl, etc.) or ar(lower)alkoxycarbonyl (e.g. benzyloxycarbonyl, etc.) and the like. The acyl group as mentioned above may contain suitable 1 to 3 substituents selected from halogen, hydroxy, cyano, nitro and the like. In addition, the reaction product of the amino group with silane, boron, phosphorus compound and the like may also act as the amino-protecting group.

When in the group —$C(R^a)(R^b)CO_2(R^c)$ for $R^2$ $R^c$ is a carboxyl-protecting group, a suitable example of the carboxyl-protecting group includes (lower)alkyl ester (e.g. methyl ester, t-butyl ester, etc.), (lower)alkenyl ester (e.g. vinyl ester, allyl ester, etc.), (lower)alkoxy(lower)alkyl ester (e.g. methoxymethyl ester, etc.), (lower)alkylthio(lower)alkyl ester (e.g. methylthiomethyl ester, etc.), halo(lower)alkyl ester (e.g. 2,2,2-trichloroethyl ester, etc.), substituted or unsubstituted aralkyl ester (e.g. benzyl ester, p-nitrobenzyl ester, etc.) or silyl ester and the like.

In preparing the reactive mixed acid anhydride of formula (I) according to the process of the present invention, the compound of formula (III) is generally used in an amount of 0.5 to 2.0 equivalent weights, preferably 1.0 to 1.3 equivalent weights, with respect to the organic acid of formula (II). In addition, the reaction may be practiced in the absence of any catalyst. However, the reaction in the absence of the catalyst requires a long reaction time and may produce some by-products. To the contrary, when the reaction is practiced in the presence of a suitable catalyst, the reaction can be completed within a short reaction time under mild conditions without formation of by-products.

Although the suitable catalyst which can be used in the present invention includes tertiary amines, quaternary ammonium or phosphonium compounds and the like, the catalyst having the optimum properties should be selected in any case since the reaction rate can be varied upon the organic acid of formula (II) as used, the kind and amount of the catalyst and the like. Examples of the tertiary amine catalyst may include 2,4-dimethyl-2,4-diazapentane, 2,5-dimethyl-2,5-diazahexane, N,N,N',N'-tetramethyl-1,2-diaminocyclohexane, 1,4-dimethyl-1,4-diazacyclohexane, 2,7-dimethyl-2,7-diaza-4-octane, 1,4-diazabicyclo[2,2,2]octane, 2,6-dimethyl-2,6-diazaheptane, 2,9-dimethyl-2,9-diazadecane, 2,5,8,11-tetramethyl-2,5,8,11-tetraazadodecane, and the like. Suitable examples of the quaternary ammonium compound may include tetra-n-butylammonium bromide, tetra-n-butylammonium chloride, cetyltrimethylammonium bromide, tetra-n-butylammonium iodide, methyl tri($C_8$–$C_{10}$)alkylammonium chloride, methyl tri-2-methylphenylammonium chloride, and the like. In addition, as the phosphonium compound tetra-n-butylphosphonium bromide is preferably used. The catalyst is used generally in the ratio of 0.1 to 50%, preferably 0.5 to 5%, on the basis of the molar amount, with respect to the organic acid of formula (II).

As a solvent in the reaction according to the present invention, a polar or non-polar organic solvent such as dichloromethane, dichloroethane, chloroform, carbon tetrachloride, toluene, xylene, acetonitrile, ethyl acetate, dioxane, tetrahydrofuran, acetone, N,N-dimethylformamide, N,N-dimethylacetamide and the like can be used. However, a mixed solvent of two or more selected from the abovementioned solvents can also be used in order to provide the optimum reactivity and the highest yield of the reaction product.

A suitable base which can be used in the present invention includes an inorganic base, for example, carbonates or hydrogen carbonates of alkaline earth metals such as sodium hydrogen carbonate, sodium carbonate, potassium hydrogen carbonate, potassium carbonate and the like; and an organic base, for example, tertiary amines such as triethylenediamine, tri-(n-butyl)amine, diisopropylethylamine, pyridine, N N-dimethylaniline, etc. Diisopropylethylamine or tri-n-butylamine is most preferably used.

In the reaction according to the present invention, the reaction temperature can be varied within a range of –40° C. to 60° C., preferably –15° C. to 25° C. Particularly, when the reaction temperature is adjusted to 0° C. to 20° C., the reaction can be completed within 1 to 4 hours to obtain easily the desired compound under mild conditions.

The reactive organic acid derivative of formula (I) as prepared according to the process of the present invention has unique physico-chemical properties. Specifically, the reactive organic acid derivative of formula (I) exhibits good solubility in a polar or non-polar organic solvent and also exhibits good stability so that it cannot be decomposed into the organic acid (II) even when the reactive organic acid derivative dissolved in such a solvent is washed with an acidic, basic or neutral water. In addition, when the reactive organic acid derivative of formula (I) is used in the acylation reaction with the amino group of β-lactam nucleus, this reaction can be readily practiced even under mild conditions and the phosphoric acid derivative produced as the by-product is present in the aqueous layer in a dissolved state and therefore can be readily removed. Accordingly, by utilizing the reactive organic acid derivative of formula (I) according to the present invention the final desired β-lactam antibiotic compound can be prepared in a high yield and in a high purity. If necessary, the compound of formula (I) according to the present invention may be prepared using the compound of formula (II) wherein the amino-protecting group is introduced into $R^1$. However, the compound of formula (I) can also be prepared from the compound of formula (II) having no protecting group without any restriction and further can also be used in the acylation reaction without any protecting group.

The present invention will be more specifically illustrated by the following examples. However, it should be understood that the scope of the present invention is not limited to these examples in any manner.

EXAMPLE 1

Synthesis of diethylthiophosphoryl (Z)-(2-aminothiazol-4-yl)methoxyimino acetate (Z)-(2-aminothiazol-4-yl)methoxyiminoacetic acid (20.1 g), tri-n-butylamine (24.10 g) and 1,4-diazabicyclo [2,2,2] octane (0.11 g) were suspended in dry dichloromethane (200 ml) and then diethylchlorothiophosphate (24.52 g) was added dropwise thereto over 20 minutes while maintaining the reaction mixture at 0° C. to 5° C. in a cooling bath under nitrogen atmosphere. The reaction mixture was stirred for a further 2 hours. After the reaction is completed, distilled water (300 ml) was added to the reaction solution and then the mixture was stirred for 5 minutes. The organic layer was separated, washed successively with 5% aqueous sodium bicarbonate solution (300 ml) and saturated saline (300 ml), dried with magnesium sulfate, filtered and then concentrated under reduced pressure. Normal hexane (400 ml) was added to the concentrated solution to solidify the product which was then filtered, washed with normal hexane (100 ml) and dried to obtain 33.2 g (Yield 94.0%) of the title compound as a pale yellow solid.

Melting Point: 87° to 88° C.

NMR (δ, $CDCl_3$): 1.38(t, 6H), 4.05(s, 3H), 4.31(m, 4H), 5.49(bs, 2H), 6.87(s, 1H)

EXAMPLE 2

Synthesis of diethylthiophosphoryl (Z)-(2-aminothiazol-4-yl)-2-(t-butoxycarbonyl)isopropoxyimino acetate (Z)-(2-aminothiazol-4-yl)-2-(t-butoxycarbonyl)isopropoxyiminoacetic acid (32.9 g), tri-n-butylamine (22.25 g) and 1,4-diazabicyclo[2,2,2]octane (0.11 g) were dissolved in dry N,N-dimethylacetamide (100 ml) and then diethylchlorothiophosphate (22.63 g) was added dropwise thereto over 20 minutes while maintaining the reaction solution at 0° C. to 5° C. in the cooling bath. The reaction mixture was stirred for a further 2 hours. Ethyl acetate (300 ml) and distilled water (300 ml) were added to the reaction solution and then the mixture was stirred for 5 minutes. The organic layer was separated, washed successively with 5% aqueous sodium bicarbonate solution (300 ml) and saturated saline (300 ml), dried with magnesium sulfate, filtered and then concentrated under reduced pressure. Cyclohexane (100 ml) was added to the concentrated solution to solidify the product which was then filtered, washed with cyclohexane (50 ml) and dried to obtain 44.26 g (Yield 92%) of the title compound as a pale white solid.

Melting Point: 114° to 115° C.

NMR (δ, $CDCl_3$): 1.39(t, 6H), 1.46(s, 9H), 1.50(s, 6H), 4.32(m, 4H), 6.74(s, 1H), 6.79(bs, 2H)

EXAMPLE 3

Synthesis of diethylthiophosphoryl (Z)-(2-aminothiazol-4-yl)ethoxyimino acetate 33.04 g (Yield 90%) of the title compound was prepared starting from (Z)-(2-aminothiazol-4-yl)ethoxyiminoacetic acid (21.5 g) according to a procedure analogous to EXAMPLE 2.

Melting Point: 118° to 119° C.

NMR (δ, CDCl₃): 1.35(m, 9H), 4.32(m, 6H), 5.67(bs, 2H), 6.82 (s, 1H)

EXAMPLE 4

Synthesis of diethylthiophosphoryl (Z)-(2-triphenylmethylaminothiazol-4-yl)ethoxyimino acetate 57.2 g of the title compound was prepared starting from (Z)-(2-triphenylmethylaminothiazol-4-yl)ethoxyiminoacetic acid (45.7 g) according to a procedure analogous to EXAMPLE 1.

Melting Point: 98° to 99° C.

NMR (δ, CDCl₃): 1.35(m, 9H), 4.32(m, 6H), 6.62(s, 1H), 7.02 (bs, 2H), 7.32 (m, 15H)

EXAMPLE 5

Synthesis of diethylthiophosphoryl (Z)-(2-triphenylmethylaminothiazol-4-yl)methoxyimino acetate 57.4 g of the title compound was prepared starting from (Z)-(2-triphenylmethylaminothiazol-4-yl)methoxyiminoacetic acid (44.3 g) according to a procedure analogous to EXAMPLE 1.

Melting Point: 101° to 103° C.

NMR (δ, CDCl₃): 1.32(m, 6H), 4.02(s, 3H), 4.28(m, 4H), 6.62(s, 1H), 7.00(bs, 1H), 7.28(m, 15H)

EXAMPLE 6

Synthesis of diethylthiophosphoryl (Z)-(2-triphenylmethylaminothiazol-4-yl)-2-(t-butoxycarbonyl)isopropoxyimino acetate 68.46 g of the title compound was prepared starting from (Z)-(2-triphenylmethylaminothiazol-4-yl)- 2-(t-butoxycarbonyl)isopropoxyiminoacetic acid (57.1 g) according to a procedure analogous to EXAMPLE 1.

Melting Point: 101° to 103° C.

NMR (δ, CDCl₃): 1.33(t, 6H), 1.41(s, 9H), 1.52(s, 6H), 4.30 (m, 4H), 6.63 (s, 1H), 6.80 (bs, 1H), 7.25 (m, 15H)

EXAMPLE 7

Synthesis of diethylthiophosphoryl (Z)-(3-amino-1,2,4-thiadiazol-5-yl)ethoxyimino acetate 33 g of the title compound was prepared starting from (Z)-(3-amino-1,2,4-thiadiazol-5-yl)ethoxyiminoacetic acid (21.6 g) according to a procedure analogous to EXAMPLE 1.

Melting Point: 132° to 133° C.

NMR (δ, CDCl₃): 1.37(m, 9H), 4.36(m, 6H), 6.49(bs, 2H)

Although this invention has been described in its preferred form with a certain degree of particularity, it is appreciated by those skilled in the art that the present disclosure of the preferred form has been made only by way of example and that numerous changes in the details of the construction, combination and arrangement of parts may be resorted to without departing from the spirit and scope of the invention.

What is claimed is:

1. A reactive thiophosphate derivative of thia(dia)zole acetic acid represented by the following general formula (I):

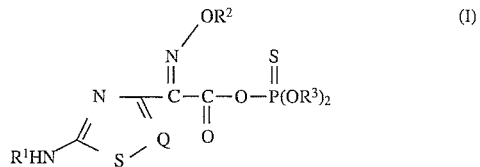

in which

R¹ represents hydrogen or an amino-protecting group;

R² represents hydrogen $C_1$–$C_4$ alkyl, or —C(Rᵃ)(Rᵇ)CO₂Rᶜ, wherein Rᵃ and Rᵇ are identical or different from each other and represent hydrogen or $C_1$–$C_4$ alkyl, or Rᵃ and Rᵇ together with a carbon atom to which they are bound form a $C_3$–$C_7$ cycloalkyl group, and Rᶜ is hydrogen or a carboxy-protecting group;

R³ represents $C_1$–$C_4$ alkyl or phenyl, or R³ together with the oxygen atom and the phosphorus atom to which it is bound forms a 5- or 6-membered heterocyclic ring; and Q represents N or CH.

2. The compound of formula (I) according to claim 1, wherein R¹ represents hydrogen or triphenylmethyl; R² represents hydrogen, methyl, ethyl or t-butoxycarbonylisopropyl; and R³ represents methyl, ethyl or phenyl.

3. The compound of formula (I) according to claim 1, wherein said compound is selected from the group consisting of:

diethylthiophosphoryl (Z)-(2-aminothiazol-4-yl)methoxyimino acetate, diethylthiophosphoryl (Z)-(2-triphenylmethylaminothiazol-4-yl)methoxyimino acetate, diethylthiophosphoryl (Z)-(2-aminothiazol-4-yl)-2-(t-butoxycarbonyl)isopropoxyimino acetate, diethylthiophosphoryl (Z)-(2-aminothiazol-4-yl)ethoxyimino acetate, diethylthiophosphoryl (Z)-(2-triphenylmethylaminothiazol-4-yl)ethoxyimino acetate, diethylthiophosphoryl (Z)-(2-triphenylmethylaminothiazol-4-yl)-2-(t-butoxycarbonyl)isopropoxyimino acetate, and diethylthiophosphoryl (Z)-(3-amino-1,2,4-thiadiazol-5-yl)ethoxyimino acetate.

4. The compound diethylthiophosphoryl (Z)-(2-aminothiazol-4-yl)methoxyimino acetate.

* * * * *